Figure 1:
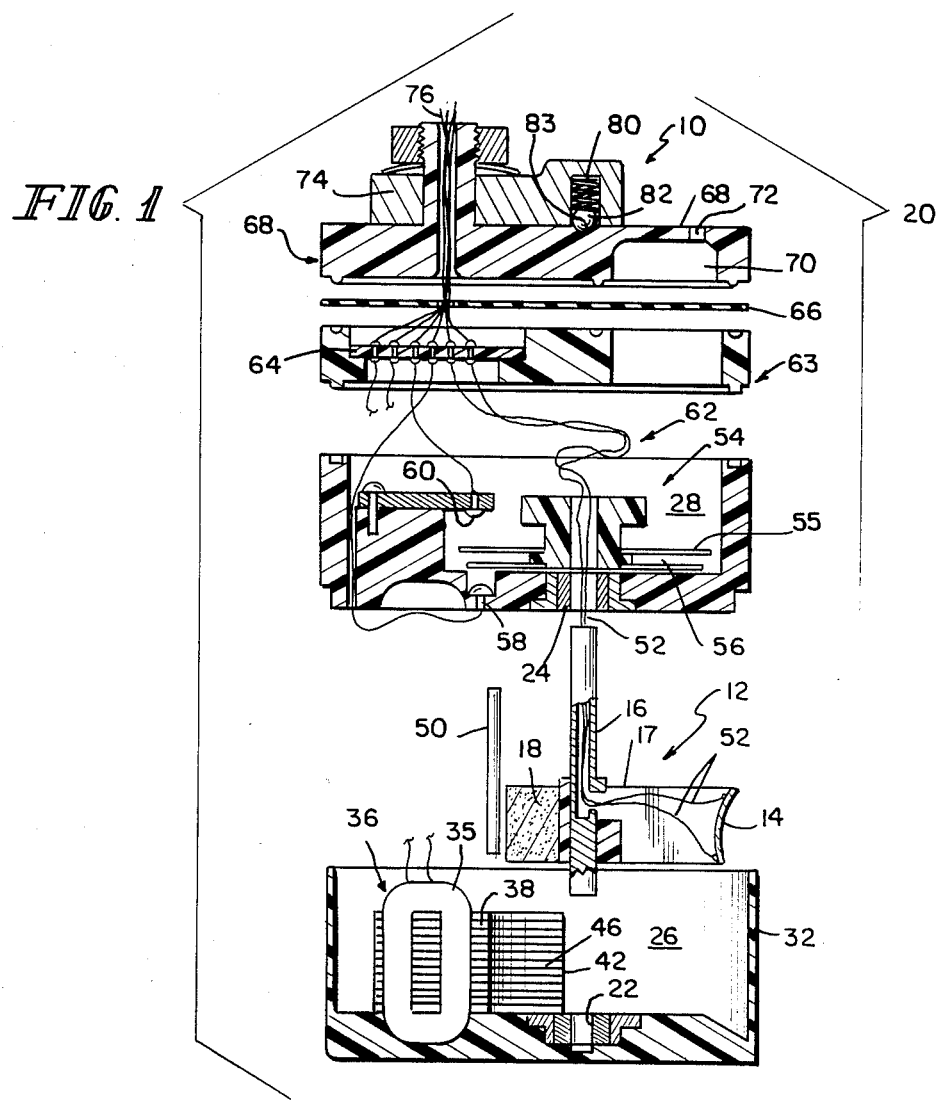

United States Patent [19]

Schroeder et al.

[11] Patent Number: 4,572,200
[45] Date of Patent: Feb. 25, 1986

[54] INTRAOPERATIVE SCANNER

[75] Inventors: Eugene Schroeder; Francis J. Fry, both of Indianapolis, Ind.

[73] Assignee: Indianapolis Center for Advanced Research, Indianapolis, Ind.

[21] Appl. No.: 600,095

[22] Filed: Apr. 13, 1984

[51] Int. Cl.$^4$ ............................................... A61B 10/00
[52] U.S. Cl. ....................................... 128/660; 73/634
[58] Field of Search ................................. 128/660–663; 73/618–620, 633, 634; 250/231 SE

[56] References Cited

U.S. PATENT DOCUMENTS

| 3,269,173 | 8/1966 | Ardenne | 128/660 |
| 4,059,098 | 11/1977 | Murdock | 128/660 |
| 4,092,867 | 6/1978 | Matzuk | 128/660 |
| 4,120,291 | 10/1978 | Paton et al. | 73/618 |
| 4,257,272 | 3/1981 | Sloman | 73/633 |
| 4,321,600 | 3/1982 | Blaser | 250/231 SE |
| 4,398,425 | 8/1983 | Matzuk | 73/634 |
| 4,399,703 | 8/1983 | Matzuk | 128/660 |
| 4,433,691 | 2/1984 | Bickman | 128/660 |
| 4,479,388 | 10/1984 | Matzuk | 73/634 |

FOREIGN PATENT DOCUMENTS 0089131 9/1983 European Pat. Off. .............. 73/618

OTHER PUBLICATIONS

Hewlett Packard 28 mm Diameter Two Channel Incremental Optical Encoder Kit HEDS-5000 Series.

Primary Examiner—Kyle L. Howell
Assistant Examiner—Ruth S. Smith
Attorney, Agent, or Firm—Barnes & Thornburg

[57] ABSTRACT

A heat-sterilizable ultrasonic surgical scanner includes an ultrasonic transducer and a permanent magnet motor for moving the transducer along an arcuate path. The scanner further includes a housing for the ultrasonic transducer and the motor. The housing includes an acoustically transparent window for transmitting ultrasonic energy from and into the housing. A resilient diaphragm permits expansion and contraction of a coupling fluid with which the housing is filled without causing fluid loss from the housing due to leakage. The resilient diaphragm is mounted at a location remote from the acoustically transparent window.

18 Claims, 3 Drawing Figures

INTRAOPERATIVE SCANNER

This invention relates to ultrasound sector scanning apparatus, and more particularly to ultrasound sector scanning systems that utilize transducers mounted for movement within predetermined paths and mounted for use during surgery.

The use of ultrasonics in a variety of testing situations has been widespread and includes the medical diagnostic and therapeutic fields. In a medical B-scan, transducers have been utilized to move along a linear path with transverse oscillation or rocking in acoustically coupled relationship with a patient to provide a "sector scan." All of the scanners heretofore used for sector scanning have been for external use only. There is a continuing need for ultrasonic imaging equipment that can be utilized in open-body surgical procedures. There are several ultrasonic scanner designs available. However, none have found wide acceptance in the operating room environment. There are a number of factors believed responsible for this lack of acceptance: (1) most of these scanners are far too large for use in an opening produced during a surgical procedure; (2) the majority of the scanners are not autoclavable, that is, not capable of withstanding the high temperatures utilized during sterilization which is required for repeated use of the scanner in such surgical procedures; (3) a large number of the scanners do not have sufficient accuracy in the controlling of the transverse oscillation or "wobble" during a scan; (4) the majority of such scanners have an insufficient field of view from which the transducer acoustical signal is directed; and finally, (5) the transducers that are now available lack the reliability necessary to be trusted in an operating room environment where open body surgical scanning is necessitated.

It is therefore an object of the present invention to provide an ultrasound sector scanner system for use in open body surgical procedures.

It is another object of the present invention to provide an ultrasound sector scanner system that is capable of withstanding high temperature sterilization to permit repeated use of the scanner in open body surgical procedures.

It is another object of the present invention to provide an ultrasonic sector scanner system that has enhanced accuracy and a broader field of view than heretofore available.

It is yet another object of the present invention to provide an ultrasonic sector scanner that is sufficiently reliable that it can be utilized in an operating room environment.

An ultrasound sector scanner system in accordance with the present invention includes a motor rotor assembly that includes an ultrasonic transducer mounted on a hollow shaft by means of an ultrasonic damping material. A small, high coercive force permanent magnet is also mounted on the hollow shaft. Flexible lead wires are coupled to the transducer and pass through the hollow shaft. The magnetic axis of the permanent magnet is aligned such that is passes through the transducer. The rotor assembly is mounted in a housing assembly which is constructed of a series of interconnecting chambers which are sealable to prevent leakage of coupling fluid utilized in the housing. The housing assembly includes a first housing component providing a window through which the ultrasonic energy is coupled. The first housing component also includes a cavity for housing a stator assembly. The motor stator includes windings and a magnetic core of a transformer-type laminations. The laminations are constructed so as to have magnetic poles at about ±45° of rotation of the rotor, to permit free rotation of said rotor within the ±45° range. By energizing the windings with current of a first polarity and then current of a second polarity, the rotor is caused to rotate approximately ±45° about the center of the window. Reversing the polarity of current through the windings oscillates the rotor in an arc about a center position, thus providing the desired sector scanning of the subject of interest. The rotation of the rotor may be limited by end stops built into the poles to provide viscous damping to aid in maintaining the ±45° limits of rotation of the rotor.

A second housing component provides a bearing for the shaft. This component also houses a digital rotor position transducer. The rotor position transducer is mounted on a portion of the shaft which extends into the second housing portion.

A digital transducer according to one aspect of the present invention uses a two-track optical encoder, with the first track being provided by a disk which is opaque over most of its area with a clear area only within the 90° angular sector (±45°) to be scanned. A system including a photoemitter on one side of the disk and a photoreceptor on the other side of the disk detects the change in opacity as the disk rotates with the shaft. Conventional circuitry (for example, an edge-triggered bistable circuit, not shown) reverses the current to the windings of the stator, thus reversing the rotation of the rotor with minimal overshoot. Upon re-illuminating of the photodetector, the position of the rotor is again obtained.

The second track of the encoder is provided with a number of equally spaced clear and opaque sections defining equal increments of rotation. Thus, with a known starting point, the position of the rotor at any instant can be determined to a high degree of accuracy and reliability. To eliminate the problems of leakage, the encoder is operated submerged in the ultrasonic coupling fluid within the housing. One housing section includes a feed-through bulkhead with molded-in electrical conductors. Contact can be made to the conductors from the motor stator, encoder, and transducer without leakage through the bulkhead's molded-in conductors. The bulkhead also serves as one retaining wall for a diaphragm formed from a high-termperature flexible material, such as a silicone, that permits expansion and contraction of the coupling fluid during operation and sterilization.

Figure 2:
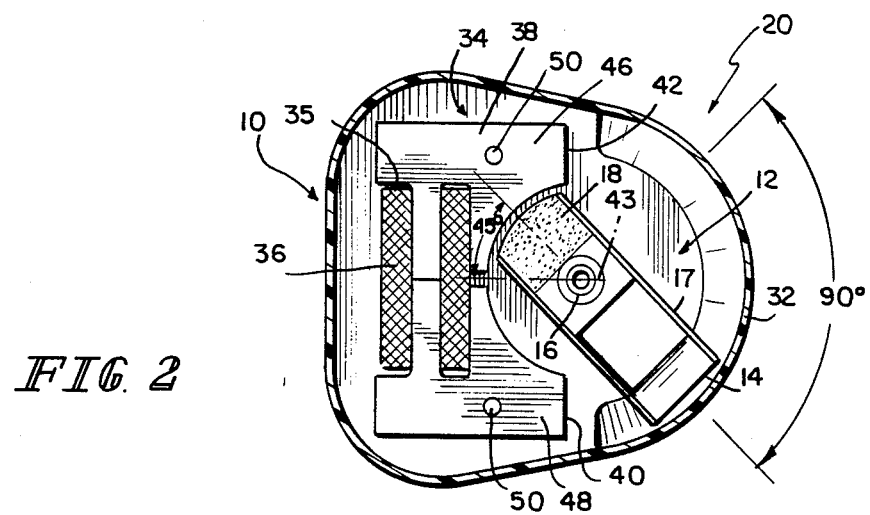
Figure 1A:
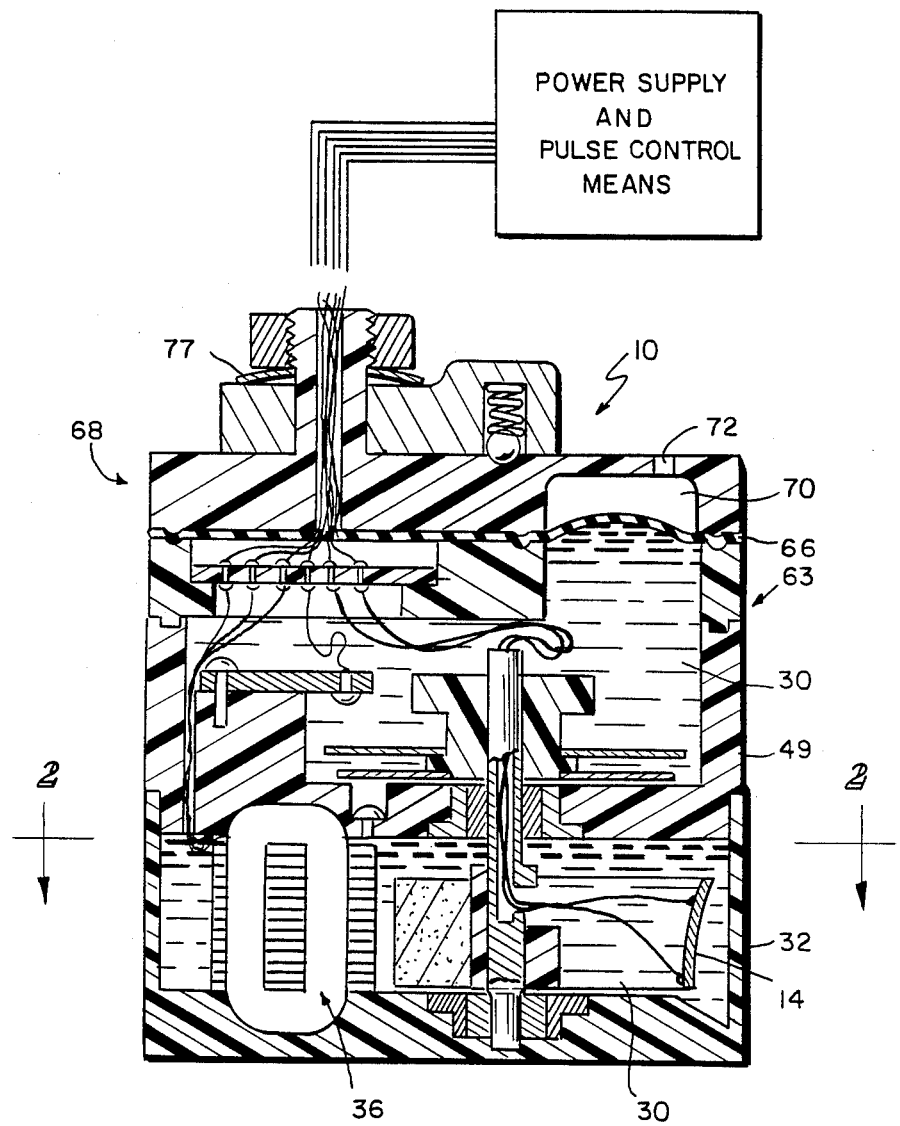

Features and advantages of the invention will become apparent to those skilled in the art upon consideration of the following detailed description of a preferred embodiment exemplifying the best mode of carrying out the invention as presently perceived. The detailed description particularly refers to the accompanying figures in which:

FIG. 1 illustrates an exploded cross-sectional view of the ultrasound sector scanner system of the present invention; FIG. 1a illustrates a sectional view of the assembled ultrasound sector scanner system of the present invention showing expansion of a coupling fluid during exposure to heat; and FIG. 2 illustrates a sectional view of the system of FIG. 1a taken generally along section lines 2—2 thereof.

Referring to FIG. 1, an ultrasound sector scanner system 10 includes a rotor assembly 12. The rotor assembly 12 is made up of an ultrasonic transducer 14 that is attached to a hollow shaft 16 by an ultrasonic damping material 17, such as Teflon-loaded epoxy. A small, high coercive force permanent magnet 18 is also attached to the shaft 16 by ultrasonic damping material. The rotor assembly 12 is mounted for rotation within a housing 20 in bearings 22 and 24. The bearings 22 and 24 permit easy rotation of the shaft 16 within the housing 20, while precluding axial motion of the shaft 16 within the housing 20. The housing 20 is constructed to include a series of interconnecting chambers including the chamber 26 housing the transducer and a chamber 28 housing an encoder. These interconnecting chambers are sealed, as will be discussed, to prevent leakage of the coupling fluid 30 that is utilized within the transducer housing 26.

The transducer chamber 26 includes a window 32 through which ultrasonic energy is coupled. This window 32 is molded into, and forms a part of, the housing 20 which is formed from a high-temperature plastic (e.g. UDEL P1700, available from Union Carbide Company). By forming the window integrally with the housing, the possibility of leakage from the window during use or sterilization is greatly reduced.

The transducer chamber 26 is suitably configured to accommodate a stator assembly 34. The stator assembly 34 includes windings 36 which are machine-wound on a bobbin 35, and a magnetic core 38 constructed from transformer-type laminations or a high-permeability ferrite. The magnetic poles 40 and 42 of the core 38 are located at about ±45° of rotation of the rotor 12 in either direction from the center 43 of the window 32.

The poles 40 and 42 permit free rotation of said rotor 12 between the ±45° positions. By energizing the coil 36 of the stator 34 with current of a first polarity, a magnetic field is established that causes the rotor 12 to move toward a position rotated approximately 45° from the center 43 of the window 32 (see FIG. 2). By reversing the current, the rotor 12 will tend to move approximately 90° to a point approximately 45° on the other side of center 43 of the window 32. By alternately reversing the polarity of current through the coils 36 of the stator 34, the rotor 12 can be made to oscillate in an approximately 90° arc about the center 43 of the window 32, thus defining a sector of the tissue of interest for scanning by the ultrasonic transducer 14.

The core 38 is configured with legs 46 and 48, the distal ends of which extend generally to the ±45° positions of rotor 12 rotation to provide the poles 40 and 42, respectively. The pole 40 and 42 faces are themselves contoured in a somewhat concave manner to conform to the transverse sectional configuration of the rotor 12. The fluid coupling medium with which cavity 26 is filled coacts with the pole 40 and 42 faces and rotor 12 to act as a snubber or shock absorber for the rotor at the endpoints of its ±45° traversals of the window 32. This promotes a smooth, shock-free deceleration of the rotor 12 near these endpoints.

Lamination locator pins 50 locate the stator 34 lamination position accurately and prevent movement of the stator assembly 34. Alternatively, the dimensions of the cavity can be such as to prevent movement of the stator assembly 34. Flexible conductors 52 with high temperature insulation, such as Teflon, are attached to the ultrasonic transducer 14 and pass through the hollow shaft 16 and the bearing 24 into chamber 28. The magnetic axis of the permanent magnet 18 is aligned so as to pass through the transducer 14. The sonic axis of the transducer 14 can be perpendicular to the axis of the shaft 16 or may be offset by, for example, 15° to reduce reflections from the window 32.

The transducer housing portion 49 which provides chamber 28, also houses a shaft position transducer 54 including an encoder 56. Any of a variety of encoders, such as optical encoders, magnetic encoders, and contact encoders, can be utilized. In the preferred embodiment, a two-track optical encoder 56 is used. One track of disk 55 of the encoder is opaque over most of its area, with a clear area only within the 90° sector to be scanned. The second track of disk 55 of the optical encoder 56 is provided with a plurality of equally spaced clear and opaque sections defining equal increments of rotation (for instance, 125 pairs of clear and opaque sections for 90° rotation, to define at least every 0.72° of rotation).

A photoemitter 58 is located on one side of the disk, and a photodetector 60 on the other side of the disk detects the changes in transmittance as the disk 55 rotates with the shaft 16. In use, conventional circuitry, such as an edge-triggered bistable circuit (not shown), responds to certain of these changes in transmittance and reverses the current to the windings 36 of the stator 34 and thus reverses the rotation of the rotor 12. The photodetector 60 will be re-illuminated following slight rotation of the rotor 12 back in the reverse direction and the position of the rotor 12 can be ascertained. By knowing the starting point of rotation and the increments of rotation from that point, the position of the rotor 12 at any time can be determined with a high degree of accuracy and reliability. By using this shaft position transducer 54 utilizing a two-track optical encoder, the transducer 14 position can be reliably determined.

To couple the transducer 14 output at maximum amplitude through window 32, and to couple reflections at maximum amplitude returning through window 32 back to transducer 14, cavity 26 is filled with a coupling fluid. To eliminate any problems of leakage of the coupling fluid, the encoder 56 is operated immersed in the coupling fluid. Degradation of the photoemitter 58 and photodetector 60 is prevented by using high-temperature hermetically sealed units with built-in lenses. Suitable units are available from Texas Instruments (the TIL-23 Series and the TIL-601 Series). The encoder disk 55 is preferably constructed using photoetching techniques in metal for low inertia and high temperature resistance.

The conductors 52 pass through the hollow shaft 16 and through the center of the encoder 56. These conductors are then wound in a loose "clock spring" coil 62 and positioned in the encoder housing cavity 28. Stresses on the conductors 52 caused by the oscillation of the transducer 14 are thus distributed over a considerable length, leading to long flex life of the conductors 52.

The chamber 28 is closed by a housing portion 63 including a feed-through bulkhead 64 through which conductors from the stator assembly 34, transducer 54, and transducer 14 are coupled by conductive terminations molded into the bulkhead, while maintaining the sealed integrity of chamber 26 and chamber 28. The housing portion 63 serves as one of the retaining walls for a resilient diaphragm 66. The diaphragm 66 is clamped between the housing portion 63 and a handle support portion 68. The diaphragm 66 permits expansion and contraction of the coupling fluid in chambers 26 and 28 during use and sterilization of the system following use. The diaphragm 66 is preferably made from a high-temperature flexible material, such as a silicone. Alternatively, diaphragm 66 can be a metal bellows. The handle support portion 68 of housing 20 defines with diaphragm 66 an expansion chamber 70 which is provided with one or more vents 72 for ventilation of the interior of the chamber 70 to the exterior. The expansion chamber 70 protects the diaphragm 66 during use and sterilization.

The handle support portion 68 is provided with a shaft extension 76 which mounts a handle assembly 74. Shaft extension 76 is hollow to permit the conductors 52 to pass from the housing 20 to external circuitry (not shown). To prevent stress to the bulkhead connections, the conductors 52 can be glued into the shaft extension 76 using a suitable high-temperature adhesive. The handle assembly 74 is pivotable about shaft extension 76. Handle assembly 74 is mounted to shaft extension 76 by sliding the shaft 76 into an opening provided on handle assembly 74, slipping a Belville washer 77 onto shaft 76 and threading a nut 78 onto the end of shaft 76, capturing the handle assembly and Belville washer on shaft 76. A spring 80-urged detent ball 82 cooperates with detent positions 83 (only one of which is shown) on the housing portion 68 to permit locking of the handle assembly 74 in various rotational orientations with respect to housing portion 68.

The coupling fluid that fills chambers 26, 28 and 63 is preferably a light grade of mineral oil. Mineral oil provides a good compromise between sonic velocity, temperature resistance, clarity, lubrication of the bearings 22 and 24, and inertness with respect to other materials to which it is exposed in chambers 26 and 28.

The system 10 thus provides an ultrasonic scanner that is accurate, can be hand-manipulated for insertion into a surgical cavity, and which is durable enough to withstand sterilization temperatures.

Although a preferred embodiment has been described, it should be recognized that changes and modifications of the elements may be made by those skilled in the art without departing from the scope or intent of the invention.

What is claimed:

1. A heat-sterilizable ultrasonic scanner comprising a housing formed to include a fluid-receiving cavity and a vent cavity in communication with both of the fluid-receiving cavity and the atmosphere, an ultrasonic transducer enclosed within the fluid-receiving cavity of the housing, coupling means for coupling ultrasonic energy from the ultrasonic transducer through the housing to a region under examination, a fluid in the fluid-receiving chamber of the housing for coupling ultrasonic energy from the ultrasonic transducer to the coupling means and vice versa, and resilient diaphragm means for permitting expansion and contraction of the coupling fluid in the fluid-receiving cavity of the housing without fluid loss therefrom during use and exposure to sterilization temperatures, said diaphragm means being mounted within the housing in spaced relation to the coupling means location to form a boundary between the fluid-receiving cavity and the vent cavity, the housing further including a wall defining a boundary of the vent cavity and substantially closing the vent cavity, the wall being formed to include an aperture interconnecting the vent cavity and the atmosphere, the wall protecting the resilient diaphragm means during sterilization and use while permitting air contained in the vent cavity to be discharged to the atmosphere via the aperture in response to movement of the resilient diaphragm means during expansion of the coupling fluid in the fluid-receiving cavity.

2. The scanner of claim 1 wherein the housing includes means for movably mounting the ultrasonic transducer within the housing.

3. The scanner of claim 2 wherein the means for movably mounting the ultrasonic transducer includes an armature for supporting the transducer for movement therewith.

4. The scanner of claim 3 wherein the housing includes means for limiting movement of the armature.

5. The scanner of claim 4 wherein the housing includes means for sensing the angular position of the armature.

6. The scanner of claim 5 wherein the housing includes means for coupling the signals from the transducer and from the means for sensing the angular position of the armature to external circuitry.

7. The scanner of claim 3 wherein the means for movably mounting said ultrasonic transducer further comprises a permanent magnet mounted on said armature, a stator mounted within said housing, and means for changing the polarity of the field of the stator such that the armature oscillates under the control of the field.

8. The scanner of claim 7 wherein the housing includes means for limiting the movement of the armature.

9. The scanner of claim 8 wherein the means for limiting the movement of the armature includes viscous damping stop means which includes means at approximately the outer limits of armature rotation.

10. The scanner of claim 9 and further comprising an optical encoder in the housing for sensing the angular position of the armature.

11. The scanner of claim 10 wherein the optical encoder comprises a first track having end points defining limits of rotation of said armature, and a second track defining increments of rotation of said armature between the limits.

12. The scanner of claim 1, wherein the resilient diaphragm means has a first cross-sectional area and the aperture has a second cross-sectional area substantially smaller than the first cross-sectional area.

13. A heat-sterilizable ultrasonic scanner comprising an ultrasonic transducer,
rotor means for rotatably mounting the ultrasonic transducer for movement along an arcuate path,
stator means for imparting rotational motion to the rotor means to move the ultrasonic transducer along the arcuate path,
a housing formed to include a liquid-receiving cavity enclosing the ultrasonic transducer, the rotor means, and the stator means, and a vent cavity communicating with the liquid-receiving cavity and the atmosphere, the housing including acoustically transparent means for transmitting ultrasonic energy from and to the liquid-receiving cavity,
a coupling fluid in the liquid-receiving cavity for conducting ultrasonic energy from and to the ultrasonic transducer, and
resilient diaphragm means forming a boundary of the liquid-receiving cavity for permitting expansion and contraction of the volume of the liquid-receiving cavity to permit expansion and contraction of the coupling fluid without fluid loss from the liquid-receiving cavity during use and exposure to sterilization temperatures, the resilient diaphragm means forming the interface between the liquid-receiving cavity and the vent cavity, the resilient diaphragm means being spaced from the acoustically transparent means, the housing further including wall means for substantially covering the resilient diaphragm means, the wall means forming the interface between the vent cavity and the atmosphere and including an aperture interconnecting the vent cavity and the atmosphere, the wall means protecting the resilient diaphragm means during use and sterilization while permitting air contained in the vent cavity to be discharged to the atmosphere via the aperture in response to movement of the resilient diaphragm means during expansion of the coupling fluid in the liquid-receiving cavity and permitting air from the atmosphere to enter the vent cavity via the aperture in response to movement of the resilient diaphragm means during contraction of the coupling fluid in the liquid-receiving cavity.

14. The scanner of claim 13, wherein the acoustically transparent means comprises a rigid housing portion.

15. The scanner of claim 13, wherein the resilient diaphragm means has a first cross-sectional area and the aperture has a second cross-sectional area substantially smaller than the first cross-sectional area.

16. The scanner of claim 13, wherein the rotor means includes an elongated armature, the ultrasonic transducer being fixed to one end of the armature, and a shaft for rotatably supporting the armature within the housing so that the ultrasonic transducer sweeps along the arcuate path during rotation of the armature.

17. The scanner of claim 16, wherein the rotor means further includes a permanent magnet fixed to the other end of the elongated armature, and the stator means includes a magnetic core assembly for conducting a magnetic field established by energizing the core assembly with an electrical current, means for applying an electrical current to the magnetic core assembly, and means for changing the polarity of the energizing electrical current to vary the magnetic field of the stator means such that the armature oscillates under the control of the field.

18. The scanner of claim 16, further comprising stop means for limiting movement of the armature along the arcuate path.

* * * * *